(12) United States Patent
Hein et al.

(10) Patent No.: US 6,995,019 B2
(45) Date of Patent: Feb. 7, 2006

(54) FLUORESCENT ISOTHIOCYANATE (FITC) SINISTRIN, ITS PRODUCTION AND USE

(75) Inventors: Heinz-Michael Hein, Weinheim (DE); Uwe Kraemer, Ilvesheim (DE); Rudolf Reiter, Weilheim (DE); Norbert Gretz, Mannheim (DE); Carsten Deus, Wiesloch (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 238 days.

(21) Appl. No.: 10/276,025

(22) PCT Filed: May 8, 2001

(86) PCT No.: PCT/EP01/05172

§ 371 (c)(1),
(2), (4) Date: Aug. 11, 2003

(87) PCT Pub. No.: WO01/85799

PCT Pub. Date: Nov. 15, 2001

(65) Prior Publication Data

US 2004/0022730 A1 Feb. 5, 2004

(30) Foreign Application Priority Data

May 11, 2000 (DE) ................ 100 23 051

(51) Int. Cl.
G01N 21/64 (2006.01)
(52) U.S. Cl. .............. 436/94; 436/166; 436/172; 600/317; 600/419; 600/420
(58) Field of Classification Search ............. 600/317, 600/419, 420; 436/56, 63, 94, 166, 172; 636/1.11, 124, 123.1
See application file for complete search history.

(56) References Cited

U.S. PATENT DOCUMENTS

| 5,561,226 | A | * | 10/1996 | Nitsch | 536/128 |
| 5,976,820 | A | * | 11/1999 | Jolley et al. | 435/7.32 |
| 6,329,531 | B1 | * | 12/2001 | Turner et al. | 548/455 |
| 6,656,451 | B1 | * | 12/2003 | Achilefu et al. | 424/9.6 |
| 6,689,616 | B1 | * | 2/2004 | Bosies et al. | 436/70 |

FOREIGN PATENT DOCUMENTS

| EP | 0568574 B1 | 11/1993 |
| EP | 0821234 A2 | 1/1998 |

OTHER PUBLICATIONS

Dorshowm R. et al "Nonivasive Fluorescence Detectionof Hepatic and Renal Function" J. Biomed. Optics, vol. 3 (1996) pp. 340-345.*

Pill, J. et al "DIrect fluorometric analysis of a newly synthesized fluorescein-labelled marker for glomerular filtration rate" Anal. Bioanal. Chem., vol. 382 (2005) pp. 59-64.*

Kuelnle, H. F. et al., "Fully Enzymatic inulin Determinationin Small Volume Samples without Deproteinization," Nephron 1992: 62: 104-107.

Lorenz, John N. et al., "A simple, nonradioactive method for evaluating single-mephron filtration rate using FITC-inulin," Special Communication, FITC-Inulin in Renal Micropuncture, pp. F172-F177, 1999.

Sohtell, Morgan et al., "FITC-inulin as a kidney tubule marker in the rat," Acta Physiol Scand 1983, 119: 313-316.

* cited by examiner

*Primary Examiner*—Jeffrey R. Snay

(57) ABSTRACT

The invention concerns fluorescein isothiocyanate-sinistrin (FITC-sinistrin), a method for its production, its use as a marker substance in a diagnostic agent and a corresponding diagnostic agent.

10 Claims, 2 Drawing Sheets

FLUORESCENT ISOTHIOCYANATE (FITC) SINISTRIN, ITS PRODUCTION AND USE

BACKGROUND OF THE INVENTION

The invention concerns a new chemical compound which can be used as a marker substance in kidney diagnostics, its production and use as well as a renal diagnostic agent containing this compound.

Fructans are used among others as marker substances in renal diagnostics and in particular to determine the glomerular filtration rate (GFR) as a test for kidney function. Fructans, which are also known as polyfructosans, are oligosaccharides and polysaccharides which are composed of straight-chained or branched fructose chains which are grafted onto a sucrose base molecule. Depending on the degree of branching of the fructose chains and on the degree of polymerization, the various fructans can have different physical properties such as different water solubilities. Many fructans occur in plants as carbohydrate reserves for example in the subterranean parts of composites, Campanulacaea, grasses and Liliacaea.

The fructans inulin and sinistrin are used in particular as marker substances in the kidney function test. Inulin and sinistrin are each composed of ca. 10 to 40 fructose units and have corresponding molecular weights of ca. 1600 to ca. 6500. After parenteral administration, inulin and sinistrin are neither changed by metabolism nor are they stored in the organism but are filtered out by the kidney glomeruli and are not reabsorbed again in the tubuli.

In order to assess renal function it is usual to determine the time course of the concentration of the marker substance in the blood after parenteral administration of a certain dose of the marker substance. The concentration of the marker substance in the blood can for example be determined by enzymatic methods (cf. e.g. H. F. Kuehnle et al., Fully enzymatic inulin determination in small volume samples without deproteinization, Nephron 62 (1992) 104–107). In the case of inulin as a marker substance, the possibility of using inulin provided with a fluorescent label such as fluroescein isothiocyanate-labelled inulin (FITC-inulin) and determining the concentration of the marker substance by measuring the fluorescence has also been described among others (cf. e.g. M. Sohtell et al., FITC-inulin as a kidney tubule marker in the rat, Acta Physiol. Scand. 119 (1983) 313–316; J. N. Lorenz & E. Gruenstein, A simple, nonradioactive method for evaluating single-nephron filtration rate using FITC-inulin, Am. J. Physiol. 276 (Renal Physiol. 45) (1999) F172–F177).

A disadvantage of inulin and FITC-inulin for the daily clinical routine is that they are only very slightly soluble in water and crystallize in aqueous preparations during storage. Hence the preparations containing inulin usually have to be heated before administration in order to redissolve the inulin or FITC-inulin. However, this procedure hydrolytically attacks the inulin depending on the duration of the heating and the inulin is partially degraded to fructose. Furthermore residues of undissolved inulin particles remain in the preparation when it is incompletely dissolved and these are difficult to detect and can result in severe circulatory complications after an injection. The low solubility of inulin and FITC-inulin make it difficult to achieve a defined concentration of the marker substance in an injection solution. Moreover the administration of inulin and FITC-inulin result in a transient reduction in blood pressure after injection into an experimental animal. In the best case this circulatory reaction lasts five minutes. The circulatory collapse impairs especially the renal function which is to be determined.

Sinistrin is a fructan like inulin and can be obtained by extraction from parts of plants containing fructan (cf. e.g. EP-B 0 568 574). However, the use of sinistrin as a marker substance requires relatively high concentrations of sinistrin in the corresponding preparations which are in a range of 100 mg per kg body weight of the individual to be examined since sinistrin itself can only be determined in blood samples and the analytical methods that are available for this are relatively insensitive. Furthermore sinistrin can only be detected by a multistep enzymatic reaction in which, after removing endogenous glucose, sinistrin is firstly converted into glucose and the glucose obtained in this manner is determined as a measure for sinistrin. Experience has shown that such multistep reactions are complicated and are often very inaccurate.

Hence the object of the present invention is to eliminate the disadvantages of the prior art. In particular an object of the present invention is to provide a substance which can be used as a marker substance in a renal function test and which has advantages over the marker substances known in the prior art and in particular inulin, FITC-inulin and sinistrin.

The object is achieved by the subject matter of the invention as stated in the patent claims.

SUMMARY OF THE INVENTION

The invention concerns sinistrin labelled with fluorescein isothiocyanate which is referred to in the following as FITC-sinistrin.

DETAILED DESCRIPTION OF THE INVENTION

Figure 1:
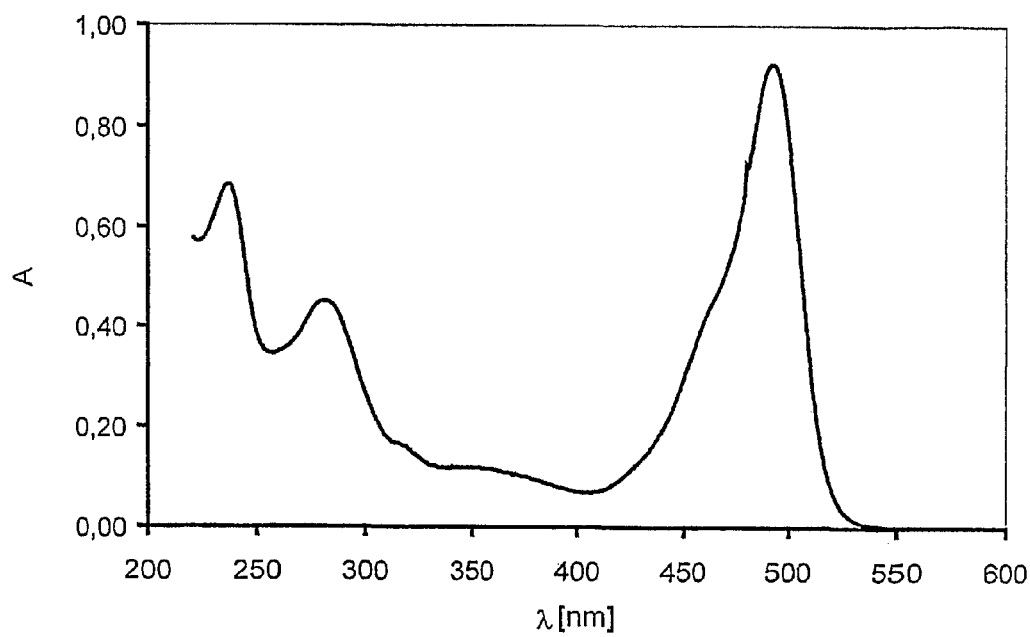
FIG. 1 shows the UV/VIS spectrum of FITC-sinistrin wherein the absorbance A is plotted against the wavelength in nm.

The FITC-sinistrin of the present invention can be obtained by reacting sinistrin with fluorescein isothiocyanate (FITC) in which the sinistrin is firstly reacted with sodium hydride (NaH) in a suitable solvent such as dimethylformamide (DMF) and subsequently FITC is added to the reaction mixture. The product, FITC-sinistrin, can be isolated as a solid by well-known methods, for example by adding aqueous ammonium chloride solution ($NH_4Cl$), subsequent extraction with diethyl ether and removal of the solvent and optionally be purified by recrystallization and/or gel filtration. A preferred preparative method for FITC-sinistrin is described in example 1.

Another subject matter of the invention is the production method for FITC-sinistrin described above.

The invention also concerns the use of FITC-sinistrin as a component of a diagnostic preparation which is especially suitable for renal diagnostics as well as a diagnostic agent, in particular a diagnostic preparation which contains FITC-sinistrin.

The FITC-sinistrin of the present invention is preferably used as a component of a preparation for a renal function test which is to be administered parenterally. In order to produce the diagnostic agent, FITC-sinistrin is dissolved in aqua ad inj. (water for injection purposes according to DAB 10) or physiological saline (isotonic sodium chloride solution). The concentration of the FITC-sinistrin in the diagnostic preparation is in the range 25 to 125 mg/ml. In addition to FITC-sinistrin the diagnostic agent to be administered parenterally can also contain physiologically tolerated buffer substances.

The presence of the fluorescein isothiocyanate group in FITC-sinistrin enables the determination of FITC-sinistrin based on measurements of fluorescence. These can be carried out in vitro for example in blood samples. The blood sample does not have to be enzymatically pretreated in order to measure the fluorescence of FITC-sinistrin in for example blood samples. Moreover the measurement of fluorescence offers the advantage of high sensitivity and speed of measurement. The measurement can be carried out with conventional standard instruments. The use of the FITC-sinistrin according to the invention as a marker substance in renal diagnostics also allows non-invasive detection methods for FITC-sinistrin. Non-invasive detection methods as used in the present terminology are methods which allow the detection of a substance, in this case of FITC-sinistrin, in tissue or body fluids without prior sampling by for example collecting blood after venepuncture or by collecting capillary blood from a finger pad or earlobe.

A fluorescence measurement procedure is preferably used as a non-invasive method for determining FITC-sinistrin in tissue or in body fluids in which light is beamed into the skin of the individual to be examined in order to excite the fluorescence and the fluorescent light emerging from the skin is detected. This can be advantageously accomplished with the aid of a non-invasive measuring head in which case a light source such as a laser emitting in the UV range illuminates the skin via glass fibre optics and excites the FITC-sinistrin molecules contained therein to fluoresce. The fluorescent light is picked up by a glass fibre optical system and measured with a corresponding detector such as a CCD spectrograph. The light source and/or the detector can be integrated into the measuring head or be arranged outside the measuring head. The measuring head is glued onto the skin of the individual to be examined for example by means of a transparent adhesive for example a transparent adhesive foil and remains there for the entire duration of the measurement.

Since it is possible to determine FITC-sinistrin with the aid of sensitive fluorescence measurements, the amount of FITC-sinistrin that is administered to the individual to be examined can be considerably less than would be the case with (underivatized) sinistrin. Whereas for sinistrin doses of 100 mg substance per kg body weight of the individual to be examined are necessary, FITC-sinistrin can already be detected with sufficient sensitivity at doses of 5 to 50 mg, preferably already even at doses of 5 to 20 mg substance per kg body weight of the individual to be examined. The low dosage considerably reduces the stress on the organism to be examined compared to sinistrin.

Moreover a non-invasive detection of FITC-sinistrin is possible. This also reduces the negative effect on the body of the individual to be examined since it is not necessary to take blood samples for the examination and determination of FITC-sinistrin.

The non-invasive measurement of the content of FITC-sinistrin can be carried out continuously over a long period, for example over the clinically relevant measuring time of 180 min for monitoring renal function (gFR). This contributes to a precise diagnosis.

Hitherto no undesired circulatory reactions have been observed in the individual examined when using FITC-sinistrin as a marker substance for the renal function test. Hence the glomerular filtration rate can be determined without a secondary effect on the kidney. This is a considerable advantage over the known use of FITC-inulin or inulin.

The present invention is further elucidated by the following examples:

EXAMPLE 1

Preparation of Fluorescein Isothiocyanate-sinistrin

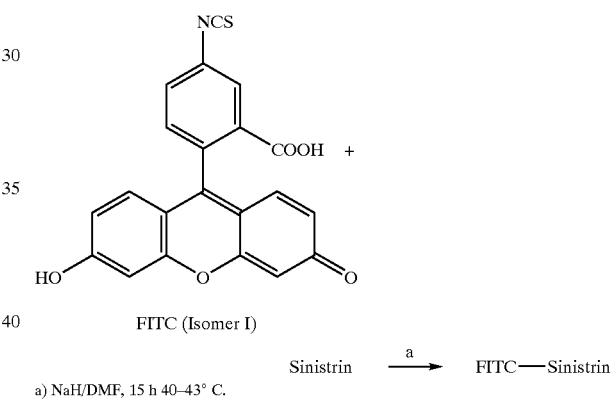

Sinistrin $\xrightarrow{a}$ FITC—Sinistrin a) NaH/DMF, 15 h 40–43° C.

Sinistrin (500 mg, 3.1 mmol/l, Fresenius Kabi, Linz, Austria) was added under a nitrogen atmosphere to 17 ml anhydrous dimethylformamide (DMF) and stirred for 15 min at 40–43° C. It was cooled in an ice bath and sodium hydride (500 mg of a 60% suspension in oil, 12.5 mmol, Fluka, Buchs, Switzerland) was added. It was stirred for 5 min at room temperature and 30 min at 40–45° C. during which the reaction mixture became increasingly viscous but remained stirrable. Fluorescein isothiocyanate (FITC, 350 mg, 0.9 mmol, Sigma, Isomer I) was added as a solid. This immediately reduced the viscosity of the reaction mixture. After 18 h stirring at 40–45° C., it was cooled to 0° C. and a solution of ammonium chloride ($NH_4Cl$, 696 mg, 13 mmol) in 10 ml water was carefully added. After adding a further 20 ml water, the turbid solution was extracted twice with diethyl ether to remove the white oil. The solvent was extensively removed on a rotary evaporator at a bath temperature of below 40° C. and the residue was dried in a high vacuum. The residue was taken up in 30 ml of a 1:1 mixture of ethanol and water and firstly precipitated with ethanol and then with acetone up to a total volume of 1000 ml. The precipitate was sedimented and centrifuged.

After a gel filtration (BioRad Biogel, P-2 extra fine, column 2.5×35 cm, eluant completely desalted water) 340 mg FITC-sinistrin was obtained as a yellow powder by a renewed precipitation.

The product contained ca. 0.14 mol FITC per 1 mol sinistrin.

FIG. 1 shows a UV/VIS spectrum of FITC-sinistrin in which the absorbance A is plotted versus the wavelength in λ nm.

EXAMPLE 2

Non-invasive Measurement of FITC-sinistrin in an Animal Experiment a) Use of the non-invasive measuring head:

The function of the non-invasive measuring head is to beam light into the skin to excite the fluorescence and to detect the fluorescent light from the skin. The measuring head was designed as a fibre optic measuring head in which an external light source (UV laser) illuminated the skin via a glass fibre and excited the FITC-sinistrin molecules contained therein. The fluorescent light (529 nm wavelength) was in turn picked up by glass fibres and measured in an external detector (CCD spectrograph).

The measuring head was glued onto the skin of the experimental animal by a transparent adhesive foil and remained there for the entire duration of the measurement.

b) Procedure for the animal experiments:

The experimental animal (rabbit) was anaesthetized in a professional manner and provided with a central arterial catheter. The catheter only served to monitor the arterial blood pressure and to remove reference blood samples.

Figure 2:
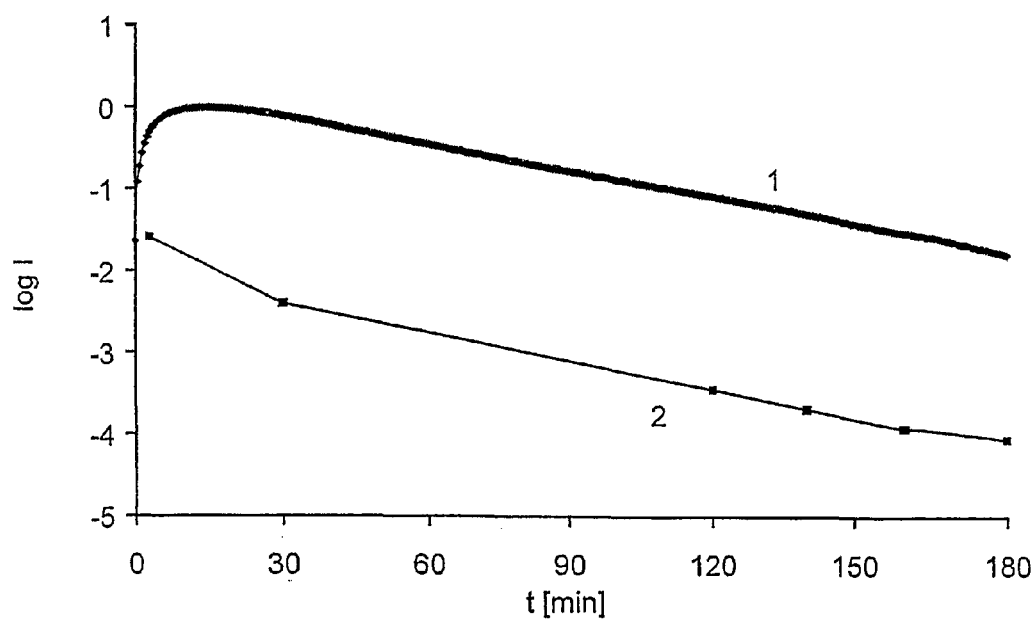
FIG. 2 shows a comparison between (1) a non-invasive clearance curve obtained by the fluorescence measurement of FITC-sinistrin and (2) a FITC-clearance curve for a fluorescence measurement in blood samples.

The non-invasive measuring head was glued onto the thorax region of the experimental animal on a shaved skin site. The test substance FITC-sinistrin was administered intravenously in a standard dose of 30 mg/kg. The total clinically relevant measuring time for the renal function test (gFR) was 180 min.

c) Result of the animal experiments:

FIG. 2 shows a comparison between a non-invasive clearance curve (1) obtained by fluorescence measurement of FITC-sinistrin and an FITC clearance curve (2) the values of which were obtained by fluorescence measurement in blood samples of the experimental animal. The standardized signal intensity I is plotted logarithmically versus the time t in min.

The agreement between the dynamics of the decrease in both curves which are also shown by the similar half-lives for clearance, indicates the equality of the two methods. In this case the half life for the non-invasive method was 38 min; 43 min was found for the invasive reference method.

EXAMPLE 3

Figure 3:
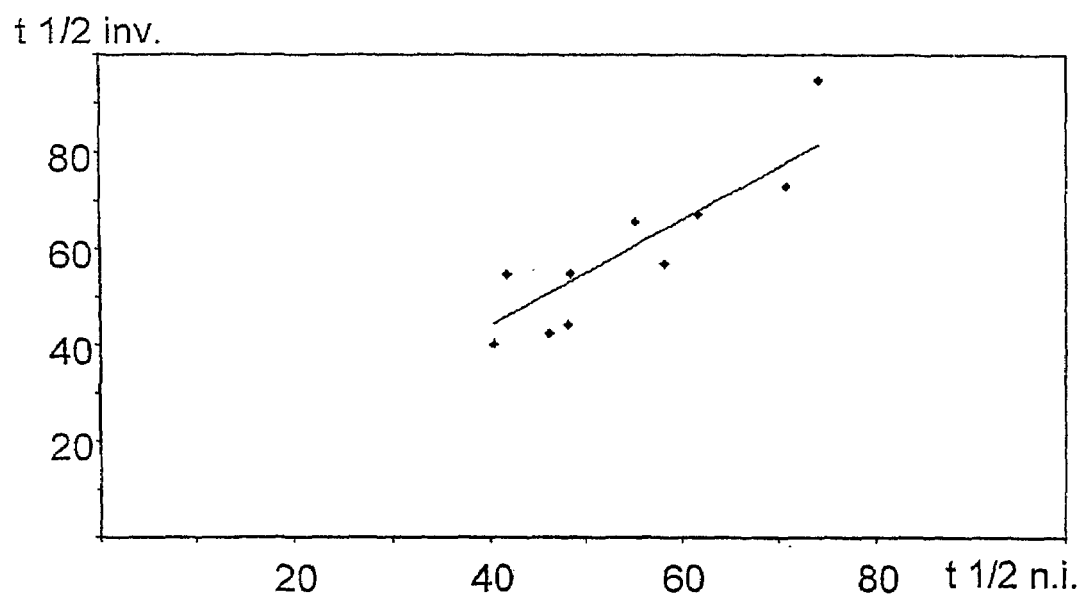
FIG. 3 shows the results of an animal experiment comparing the half-lives (in minutes) for the clearance curves of FITC-sinistrin obtained from invasive measurements (t ½ inv.) plotted against the half lives obtained from non-invasive measurements (t ½ n.i.).

Comparison of an Invasive with a Non-invasive Measuring Method for Sinistrin and Inulin The animal experiment from example 2 was repeated 10 times in an identical manner for FITC-sinistrin. The half-lives (in minutes) for the clearance curves obtained from the invasive measurements (t ½ inv.) were plotted against the half-lives obtained from the non-invasive measurements (t ½ n.i.). The results are shown in FIG. 3. The correlation coefficient was 89.9%.

Figure 4:
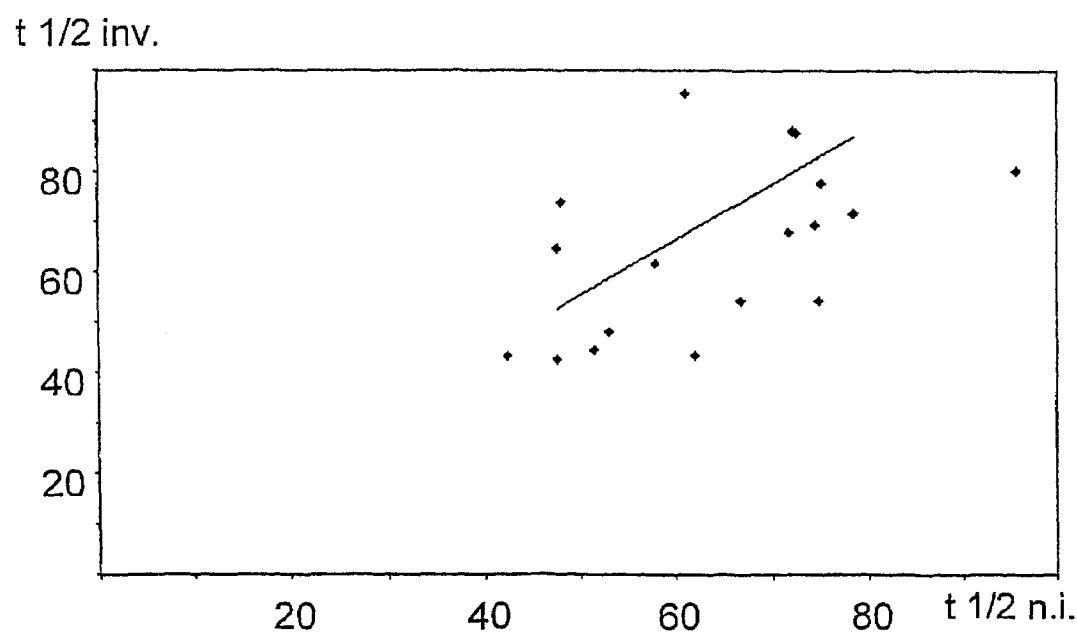
FIG. 4 shows the results of an animal experiment comparing the half-lives (in minutes) for the clearance curves of FITC-inulin obtained from invasive measurements (t ½ inv.) plotted against the half lives obtained from non-invasive measurements (t ½ n.i.).

The animal experiment from example 2 for FITC-inulin (obtainable from Sigma (Aldrich)) was repeated 20 times in an identical manner as a comparison. The half-lives (in minutes) for the clearance curves obtained from the invasive measurement (t ½ inv.) were plotted against the half-live measurements. The results are shown in FIG. 4. The correlation coefficient was only 49.2% in this case.

Whereas a very good correlation was found between invasive and non-invasive measurement when using the FITC-sinistrin according to the invention, almost no correlation is observed for FITC-inulin. The poor agreement in the case of FITC-inulin is possibly due to the fact that the physiology of the experimental animal is disturbed by FITC-inulin to such an extent that a proper measurement is not possible. This problem does not occur with the FITC-sinistrin according to the invention.

EXAMPLE 4

Differences in the Accumulation of FITC-sinistrin and FITC-inulin in the Organs of Experimental Animals A rat was administered 30 mg FITC-sinistrin per kg body weight at intervals of 2 days. 4 hours after the last administration of FITC-sinistrin the animal was sacrificed and organ sections of the lung, liver and kidney of the experimental animal were prepared. The sections were examined by fluorescence measurement for the presence of FITC-sinistrin. In none of the said organs was fluorescence found above the extent of self fluorescence. Hence all organs were free of FITC-sinistrin.

An identical experiment was carried out with FITC-inulin. In this case considerable fluorescence is observed in the said organs liver, lung and kidneys which is due to the presence of FITC-inulin.

In the liver FITC-inulin was mainly found intracellularly. This causes irreversible cell damage (cell death) and can lead to long-term damage to the organ. FITC-inulin was found in the corpuscles in the lung which leads to microstenoses and ultimately to embolism.

Even in rats which were sacrificed 6 minutes after the injection and were immediately rinsed with saline solution in order to remove all blood etc. from the animal, it was observed that, when FITC-inulin is used, this substance accumulates in the liver, lung and kidneys. Hence in this experiment quantities of FITC-inulin were found which are very quickly deposited in the organs. In contrast fluorescence was found in none of the above-mentioned organs when FITC-sinistrin was administered.

EXAMPLE 5

Detection of FITC-sinistrin by Means of Test Strips

A two layer coating of the coating compositions 1 and 2 described in the following was applied to a 125 µm thick transparent Pokalon foil as described in EP-A 0 821 234 which had been pretreated by Corona treatment. The layers were each successively knife-coated in a thickness of 75 µm (firstly coating composition 1) at a speed of 1 m/min; the layers being dried for 30 min at 50° C. after each coating. The films obtained in this manner were cut into pieces of 6 mm×6 mm in size and glued onto a 100 mm long, 6 mm wide and 1 mm thick polyester foil over a circular hole of 4 mm diameter using a double adhesive tape which essentially served the purpose of facilitating the handling of the test strip. In this process the Pokalon foil of the coated film was placed on the adhesive tape such that the film layer consisting of the coating composition 2 remained accessible for sample application. The adhesive tape also had a hole of 4 mm diameter at the site at which the polyester foil had a hole.

10 μl of a sample solution was applied to the test strips manufactured in this manner (on the open side of the two layer film) and measured from the underside (Pokalon foil) by means of a conventional fluorescence detection instrument. The measured fluorescence at 520 nm correlated excellently with the amount of FITC-sinistrin in the sample.

| Coating composition 1 (amounts are stated in g per 100 g final composition) | |
|---|---|
| Keltrol (1.4% in water) | 34.116 |
| Transpafill solution (21.2% in water) | 41.069 |
| Propiofan 70 D | 4.347 |
| PVP solution (14,117 g water + 0.290 g Mega 8 + 0.041 Geropon T77) | 14.449 |
| Hexanol | 0.221 |
| Methoxypropanol | 5.824 |

| Coating composition 2 (amounts are stated in g per 100 g final composition) | |
|---|---|
| Gantrez S97 (4% in water; adjusted to pH 7 with 16% NaOH) | 49.039 |
| TiO2 slurry (50% in water) | 38.871 |
| Propiofan 70 D | 3.880 |
| PVP solution (7.909 g water + 0.390 g Mega 8 + 0.040 Geropon T77) | 8.339 |
| Hexanol | 0.215 |
| Methoxypropanol | 5.676 |

In general it should be noted for the FITC-sinistrin detection by test strips (or test elements that are not in a test strip shape such as essentially rectangular slides) that an absorbent matrix should be preferably present that is for example made of cellulose or—as in the above example—of an absorbent polymer or polymer mixture. The film matrix can be a monolayer or multilayer e.g. composed of a polymer plus an organic constituent. The films preferably contain no conventional detection enzymes and detection reagents (as is the case in conventional test strips) since it is only intended to measure the fluorescence of the sample. To this extent it is important that the basic substances used to manufacture the test elements for the FITC-sinistrin test by means of fluorescence do not exhibit self-fluorescence or as little as possible.

Since the fluorescence depends on the protein concentration of the sample it may be advantageous to combine a fluorescence measurement for determining FITC-sinistrin with a protein measurement on one test strip such as that known from urine test strips. Optionally a test for haemoglobin as an exclusion criterion should be carried out alternatively or in addition since haemolytic samples have to be discarded. Haemoglobin determination by means of test strips is also known for example from urine test strips. The determination of the said parameters is preferably carried out by means of test strips which have several specific test fields for the respective parameters.

The invention claimed is:

1. A method for producing fluorescein isothiocyanate-sinistrin (FITC-sinistrin) comprising:
   (a) reacting sinistrin with sodium hydride in a solvent to form a reaction mixture;
   (b) adding FITC to the reaction mixture; and
   (c) isolating FITC-sinistrin as a solid.

2. The method of claim 1 wherein the solvent is anhydrous dimethylformamide.

3. The method of claim 1 wherein the FITC-sinistrin is isolated by adding an aqueous ammonium chloride solution to the reaction mixture, extracting the FITC-sinistrin with diethyl ether and removing the diethyl ether to isolate solid FITC-sinistrin.

4. The method of claim 3 wherein the solid FITC is purified by at least one of recrystallization and gel filtration.

5. Fluorescein isothiocyanate-sinistrin (FITC-sinistrin) obtainable by the method of claim 1.

6. A composition comprising fluorescein isothiocyanate-sinistrin (FITC-sinistrin) in a physiologically acceptable solution.

7. The composition of claim 6 wherein the solution comprises FITC-sinistrin in a concentration of 25–125 mg/ml.

8. A method for measuring renal function in a patient comprising:
   administering to the patient a FITC-sinistrin;
   beaming light onto the skin of the patient; and
   detecting the fluorescent light emitted from the skin wherein the amount of fluorescence is related to the renal function of the patient.

9. The method of claim 8 wherein the FITC-sinistrin is prepared by the method of claim 9.

10. The method of claim 8 wherein the FITC-sinistrin is administered in a dose of 5–50 mg/kg.

* * * * *